US008965488B2

(12) United States Patent
Dvorsky et al.

(10) Patent No.: US 8,965,488 B2
(45) Date of Patent: Feb. 24, 2015

(54) METHOD FOR EVALUATING BLUSH IN MYOCARDIAL TISSUE (71) Applicant: Novadaq Technologies Inc., Mississauga (CA)

(72) Inventors: Peter Dvorsky, Toronto (CA); David Mark Henri Goyette, Mississauga (CA); T. Bruce Ferguson, Jr., Raleigh, NC (US); Cheng Chen, Greenville, NC (US)

(73) Assignee: Novadaq Technologies Inc., Mississauga (CA)

( * ) Notice: Subject to any disclaimer, the term of this patent is extended or adjusted under 35 U.S.C. 154(b) by 0 days.

(21) Appl. No.: 13/850,063

(22) Filed: Mar. 25, 2013

(65) Prior Publication Data

US 2013/0217985 A1 Aug. 22, 2013

Related U.S. Application Data (60) Division of application No. 12/841,659, filed on Jul. 22, 2010, now Pat. No. 8,406,860, which is a continuation-in-part of application No. PCT/CA2009/000073, filed on Jan. 23, 2009.

(60) Provisional application No. 61/023,818, filed on Jan. 25, 2008, provisional application No. 61/243,688, filed on Sep. 18, 2009.

(51) Int. Cl.
*A61B 6/00* (2006.01)
*A61B 5/00* (2006.01)
(Continued)

(52) U.S. Cl.
CPC ............ *A61B 5/0261* (2013.01); *A61B 5/0059* (2013.01); *A61B 6/503* (2013.01);
(Continued)

(58) Field of Classification Search
CPC .... A61B 5/0059; A61B 5/0261; A61B 5/489; A61B 5/7225; A61M 5/007
USPC .......................... 600/312, 317, 329, 363, 476
See application file for complete search history.

(56) References Cited

U.S. PATENT DOCUMENTS

| 4,162,405 A | 7/1979 | Chance et al. |
| 6,093,149 A | 7/2000 | Guracar et al. |

(Continued)

FOREIGN PATENT DOCUMENTS

| CN | 1399528 A | 2/2003 |
| DE | 39 06 860 A1 | 9/1989 |

(Continued)

OTHER PUBLICATIONS

Azijma et al. "Detection of Skin Perforators by Indocyanine Green Fluorescence Nearly Infrared Angiography." Oct. 2008, pp. 1062-1067.

(Continued)

*Primary Examiner* — Michael Rozanski
(74) *Attorney, Agent, or Firm* — Oliff PLC (57) ABSTRACT

Vessel perfusion and myocardial blush are determined by analyzing fluorescence signals obtained in a static region-of-interest (ROI) in a collection of fluorescence images of myocardial tissue. The blush value is determined from the total intensity of the intensity values of image elements located within the smallest contiguous range of image intensity values containing a predefined fraction of a total measured image intensity of all image elements within the ROI. Vessel (arterial) peak intensity is determined from image elements located within the ROI that have the smallest contiguous range of highest measured image intensity values and contain a predefined fraction of a total measured image intensity of all image elements within the ROI. Cardiac function can be established by comparing the time differential between the time of peak intensity in a blood vessel and that in a region of neighboring myocardial tissue both pre and post procedure.

10 Claims, 12 Drawing Sheets (51) Int. Cl.
  *A61B 5/026* (2006.01)
  *A61M 5/00* (2006.01)
(52) U.S. Cl.
  CPC .............. *A61B 5/489* (2013.01); *A61B 5/7225* (2013.01); *A61M 5/007* (2013.01); *A61B 6/504* (2013.01); *A61B 6/507* (2013.01)
  USPC ........... 600/476; 600/312; 600/317; 600/329; 600/363

(56) References Cited

U.S. PATENT DOCUMENTS

| | | |
|---|---|---|
| 6,621,917 B1 | 9/2003 | Vilser |
| 6,631,286 B2 | 10/2003 | Pfeiffer et al. |
| 6,915,154 B1 | 7/2005 | Docherty et al. |
| 2002/0099279 A1 | 7/2002 | Pfeiffer et al. |
| 2002/0183621 A1 | 12/2002 | Pfeiffer et al. |
| 2003/0032885 A1 | 2/2003 | Rubinstein et al. |
| 2003/0064025 A1 | 4/2003 | Yang et al. |
| 2004/0066961 A1 | 4/2004 | Spreeuwers et al. |
| 2004/0162489 A1 | 8/2004 | Richards-Kortum et al. |
| 2005/0019744 A1 | 1/2005 | Bertuglia |
| 2005/0020891 A1 | 1/2005 | Rubinstein et al. |
| 2005/0182327 A1 | 8/2005 | Petty et al. |
| 2005/0182434 A1 | 8/2005 | Docherty et al. |
| 2006/0079750 A1 | 4/2006 | Fauci et al. |
| 2006/0147897 A1 | 7/2006 | Grinvald et al. |
| 2007/0254276 A1 | 11/2007 | Deutsch et al. |
| 2008/0071176 A1 | 3/2008 | Docherty et al. |
| 2009/0005693 A1 | 1/2009 | Brauner et al. |
| 2009/0048516 A1 | 2/2009 | Yoshikawa et al. |
| 2010/0036217 A1 | 2/2010 | Choi et al. |

FOREIGN PATENT DOCUMENTS

| | | |
|---|---|---|
| DE | 101 20 980 A1 | 11/2002 |
| JP | A-H09-308609 | 12/1997 |
| JP | A-2003-510121 | 3/2003 |
| JP | A-2004-528917 | 9/2004 |
| JP | A-2006-192280 | 7/2006 |
| JP | A-2007-21006 | 2/2007 |
| JP | A-2008-525126 | 7/2008 |
| JP | A-2008-231113 | 10/2008 |
| RU | 2288633 C1 | 12/2006 |
| WO | WO 01/08552 A1 | 2/2001 |
| WO | WO 01/22870 A1 | 4/2001 |
| WO | WO 01/80734 A1 | 11/2001 |
| WO | WO 01/82786 A2 | 11/2001 |
| WO | WO 2004/052195 A1 | 6/2004 |
| WO | WO 2005/079238 A2 | 9/2005 |
| WO | WO 2006/123742 A1 | 11/2006 |
| WO | WO 2009/048660 A2 | 4/2009 |
| WO | WO 2009/092162 A1 | 7/2009 |
| WO | WO 2009/127972 A2 | 10/2009 |

OTHER PUBLICATIONS

Detter, C. et al. "Fluorescent Cardiac Imaging: A Novel Intraoperative Method for Quantitative Assessment of Myocardial Perfusion During Graded Coronary Artery Stenosis." Circulation, Aug. 1, 2007, pp. 1007-1014, vol. 116, No. 9.

Detter, C. et al. "Near-Infrared Fluorescence Coronary Angiography: A New Noninvasive Technology for Intraoperative Graft Patency Control." The Heart Surgery Forum, Jun. 2011, pp. 364-369, vol. 5, Issue 4.

Forrester et al. "Comparison of Laser Speckle and Laser Doppler Perfusion Imaging: Measurement in Human Skin and Rabbit Articular Tissue," Medical and Biological Engineering and Computing, Nov. 1, 2002, pp. 687-697, vol. 40, No. 6.

Frenzel H. et al. "In vivo perfusion analysis of normal and dysplastic ears and its implication on total auricular reconstruction." Journal of Plastic, Reconstructive and Aesthetic Surgery, Apr. 18, 2008, pp. S21-S28, vol. 61.

Holm, et al. "Intraoperative evaluation of skin-flap viability using laser-induced fluorescence of indocyanine green." British Journal of Plastics Surgery, Dec. 1, 2002, pp. 635-644, vol. 55, No. 8.

Holm et al. "Laser-Induced Fluorescence of Indocyanine Green: Plastic Surgical Applications." European Journal of Plastic Surgery, Feb. 25, 2003, pp. 19-25, vol. 26.

Holm et al. "Monitoring Free Flaps Using Laser-indeuced Fluorescence of Indocyanine Green: A Preliminary Experience." Wiley Interscience, 2002, pp. 278-287.

Jolion, J. et al. "Robust Clustering with Applications in Computer Vision." IEEE Transactions on Pattern Analysis and Machine Intelligence, Aug. 1991, pp. 791-802, vol. 13, No. 8.

Krishnan K. G. et al. "The role of near-infrared angiography in the assessment of postoperative veneous congestion in random pattern, pedicled island and free flaps." British Journal of Plastic Surgery, Apr. 1, 2005, pp. 330-338, vol. 58, No. 3.

Martinez-Perez, M. et al. "Unsupervised Segmentation Based on Robust Estimation and Cooccurrence Data." Proceedings of the International Conference on Miage Processing (ICIP) Lausanne, Sep. 19, 1996, pp. 943-945, vol. 3.

"Novadaq Imaging System Receives FDA Clearance for use During Plastic Reconstructive Surgery." PR Newswire, Jan. 29, 2007, 3 pages.

Newman et al. "Update on the Application of Laser-Assisted Indocyanine Green Fluorescent Dye Angiography in Microsurgical Breast Reconstruction." Oct. 31, 2009, 2 pages.

Pandharipande et al. "Perfusion Imaging of the Liver: Current Challenges and Future Goals." Radiology, 2005, pp. 661-673.

Sezgin, M. et al. "Survey over image thresholding techniques and quantitative performance evaluation." Journal of Electronic Imaging, Jan. 2004, pp. 146-165, vol. 13(1).

Verbeek, X. "High-Resolution Functional Imaging With Ultrasound Contrast Agents Based on RF Processing in an Un Vivo Kidney Experiment." Ultrasound in Med. & Biol., 2001, pp. 223-233, vol. 27, No. 2.

Yamaguchi et al. "Evaluation of Skin Perfusion After Nipple-Sparing Mastectomy by Indocyanine Green Dye." (With English Abstract) Journal of Saitama Medical University, Japan, Apr. 2005, pp. 45-50, vol. 32, No. 2.

Jan. 25, 2012 International Search Report issued in Application No. PCT/IB11/002381.

Jul. 3, 2012 Translation of Chinese Office Action issued in Chinese Application No. 200980123414.0.

Mar. 29, 2013 Translation of Russian Office Action issued in Russian Application No. 2011111078/14.

May 23, 2013 Translation of Chinese Office Action issued in Chinese Application No. 200980123414.0.

May 30, 2013 Mexican Office Action issued in Mexican Application No. MX/a/2010/011249.

Jul. 29, 2013 Translation of Russian Decision on Grant issued in Russian Application No. 2011111078/14.

Jul. 30, 2013 Translation of Japanese Office Action dated Jul. 30, 2013 issued in Japanese Application No. 2011-504574.

May 15, 2014 Supplemental European Search Report and Written Opinion issued in European Application No. 09 732 993.2.

METHOD FOR EVALUATING BLUSH IN MYOCARDIAL TISSUE

CROSS-REFERENCE TO RELATED APPLICATIONS

This application is a divisional of co-pending U.S. application Ser. No. 12/841,659, filed Jul. 22, 2010 which is a continuation-in-part of PCT International Application Number PCT/CA2009/000073, filed Jan. 23, 2009, which designated the United States and has been published as International Publication No. WO 2009/092162 in the English language, and which claims the benefit of U.S. Provisional Application No. 61/023,818, filed Jan. 25, 2008, the entire contents of which are incorporated herein by reference. This application also claims the benefit of prior filed U.S. Provisional Application No. 61/243,688, filed Sep. 18, 2009, the entire contents of which are incorporated herein by reference.

BACKGROUND OF THE INVENTION

The invention relates to a method for evaluating myocardial blush in tissue from images recorded following injection of fluorescent dyes.

TIMI (Thrombolysis In Myocardial Infarction) studies initially suggested that successful restoration of flow in an infarcted artery was the major goal of reperfusion. However, substantial evidence has grown over the years showing that distortion of microvasculature and myocardial perfusion is often present despite epicardial artery patency. This might be the result of a combination of distal embolization and reperfusion injury with cellular and extracellular edema, neutrophil accumulation and release of detrimental oxygen free radicals.

Myocardial blush was first defined by van't Hof et al. as a qualitative visual assessment of the amount of contrast medium filling a region supplied by an epicardial coronary artery. It is graded as Myocardial Blush Grade: 0 (=no myocardial blush or contrast density), 1 (=minimal myocardial blush or contrast density), 2 (=myocardial blush or contrast density which exists to lesser extent and its clearance is diminished compared to non-infarct-related coronary artery), and 3 (=normal myocardial blush or contrast density comparable with that obtained during angiography of a contralateral or ipsilateral non-infarct-related coronary artery). When myocardial blush persists (long "wash-out rate" or "staining"), it suggests leakage of the contrast medium into the extravascular space or impaired venous clearance and is graded 0.

The consequences of microvascular damage are extremely serious. In patients treated with thrombolytics for acute myocardial infarction, impaired myocardial perfusion as measured by the myocardial blush score corresponds to a higher mortality, independent of epicardial flow. Myocardial blush grade correlates significantly with ST segment resolution on ECGs, enzymatic infarct size, LVEF, and is an independent predictor of long-term mortality. Myocardial blush grade may be the best invasive predictor of follow-up left ventricular function. Determining the myocardial blush has emerged as a valuable tool for assessing coronary microvasculature and myocardial perfusion in patients undergoing coronary angiography and angioplasty.

The degree of blush that appears during imaging (e.g., imaging with a fluorescent dye, such as ICG) is directly related to the underlying tissue perfusion. Conventionally, to quantitatively characterize kinetics of dye entering the myocardium using the angiogram, digital subtraction angiography (DSA) has been utilized to estimate the rate of brightness (gray/sec) and the rate of growth of blush (cm/sec). DSA is performed at end diastole by aligning cine frame images before the dye fills the myocardium with those at the peak of a myocardial filling to subtract spine, ribs, diaphragm, and epicardial artery. A representative region of myocardium is sampled that is free of overlap by epicardial arterial branches to determine the increase in the grayscale brightness of the myocardium at peak intensity. The circumference of the myocardial blush is then measured using a handheld planimeter. The number of frames required for the myocardium to reach peak brightness is converted into time by dividing the frame count by the frame rate. This approach is quite time-consuming and is difficult to perform on a beating heart and to conclude within a reasonable time.

Generally, conventional techniques gathering statistical information about a ROI rely on algorithms that track the ROI during movement of the underlying anatomy and attempt to keep the ROI localized in the same tissue portion. For example, the user can draw an initial ROI in the image, ignoring any blood vessels not to be included in the calculation, with the initial ROI then adjusted to the moving anatomy through linear translation, rotation, and distortion. However, this approach is computationally intensive and not reliable with low contrast images.

Accordingly, there is a need for a method to determine blush of myocardial tissue while the heart is beating, to eliminate effects from features other than myocardial tissue that may migrate into the region of interest (blood vessels, clips, the surgeon's hands, etc . . . ), and to produce useful information for the surgeon during a medical procedure within a "reasonable time," if not within "real time."

There is also a need for measuring improvement in cardiac function by measuring the time differential between when contrast in a blood vessel reaches its peak intensity and when the contrast in a neighboring region in the myocardial tissue reaches its corresponding peak. If this time differential decreases after a medical procedure as compared to before the procedure, under uniform hemodynamic conditions cardiac function can be said to have improved. A method for tracking blood vessels during image acquisition improves our ability to locate the time at which the contrast in a blood vessel achieves its peak intensity.

SUMMARY OF THE INVENTION

The present invention is directed to a method for evaluating myocardial blush in tissue from images recorded following injection of fluorescent dyes using a static ROI (Region-of-Interest) that is fixed in position on the image while the heart (or other tissue of interest) moves under it in the image sequence. The static ROI uses a statistical technique to eliminate intensity outliers and to evaluate only those pixels that have less inter-pixel intensity variance. The technique is highly robust, and the results depend only insignificantly on changes to the ROI size and position, providing the ROI is placed in the same general region of the anatomy.

According to one aspect of the invention, a method for determining perfusion in myocardial tissue using fluorescence imaging, includes the steps of defining a static region of interest (ROI) in an image of the myocardial tissue, measuring fluorescence intensity values of image elements (pixels) located within the ROI, and determining a blush value from an average of the intensity values of image elements located within a smallest contiguous range of image intensity values containing a first predefined fraction of a total measured image intensity of all image elements within the ROI.

Advantageous embodiments may include one or more of the following features. The smallest range of contiguous image intensity values may be determined from a histogram of a frequency of occurrence of the measured image intensity values, wherein the first predefined fraction may be between 70% and 30%, preferably between 60% and 40%, and most preferably at about 50%. Blush values are determined, optionally continuously, over a predefined period of time. At least one of the blush rate and the washout rate may be determined from the slope of the time-dependent blush values.

Alternatively or in addition, the blush and associated perfusion may be determined by defining a second static ROI in the image of the myocardial tissue, with the second ROI including an arterial blood vessel, and determining a measure of the peak intensity of the arterial blood vessel from a total intensity of the intensity values of image elements located within a smallest contiguous range of high image intensity values containing a second predefined fraction, for example 20%, of a total measured image intensity of brightest image elements within the ROI. This measurement can then be used to determine an outcome of a procedure by comparing an elapsed time between a maximum blush value and maximum measure of perfusion before the procedure and an elapsed time between a maximum blush value and maximum measure of perfusion after the procedure.

According to another aspect of the invention, a method for tracking a blood vessel in an image includes the steps of (a) acquiring a fluorescence image of tissue containing a blood vessel, (b) delimiting a segment of the blood vessel with boundaries oriented substantially perpendicular to a longitudinal direction of the blood vessel, (c) constructing at least one curve extending between the delimiting boundaries and located within lateral vessel walls of the blood vessel, wherein the at least one curve terminates at the delimiting boundaries substantially perpendicular to the boundaries, and (d) determining a fluorescence signal intensity in the fluorescence image along the at least one curve, with the signal intensity being representative of vessel perfusion.

In one exemplary embodiment, the at least one curve may be defined by a spline function. For example, more than one curve may be constructed and the fluorescence signal intensity may be determined by averaging the signal intensity from points on the curves having a substantially identical distance from one of the delimiting boundaries.

Advantageously, the position of the lateral vessel walls in the fluorescence image may be determined using an edge-detection algorithm, such as a Laplacian-of-a-Gaussian operator.

In another exemplary embodiment, time-sequential fluorescence images of the tissue containing the blood vessel may be acquired. Characteristic dimensions of the delimited segment may then be determined from the location of the lateral vessel walls in the first image, and positions of lateral vessel walls may be determined in at least one second image. The characteristic dimensions from the first image may then be matched to the positions of lateral vessel walls in the second image to find a location of the lateral vessel walls of the first image in the at least one second image. The steps (c) and (d) above are then repeated for the second image or images.

Advantageously, an average fluorescence signal intensity of all points may be computed along the curve and a change in perfusion of the blood vessel may be determined from a change in the average fluorescence signal intensity between the time-sequential images.

These and other features and advantages of the present invention will become more readily appreciated from the detailed description of the invention that follows and from the appended drawings.

DETAILED DESCRIPTION OF EXEMPLARY EMBODIMENTS

Figure 1:
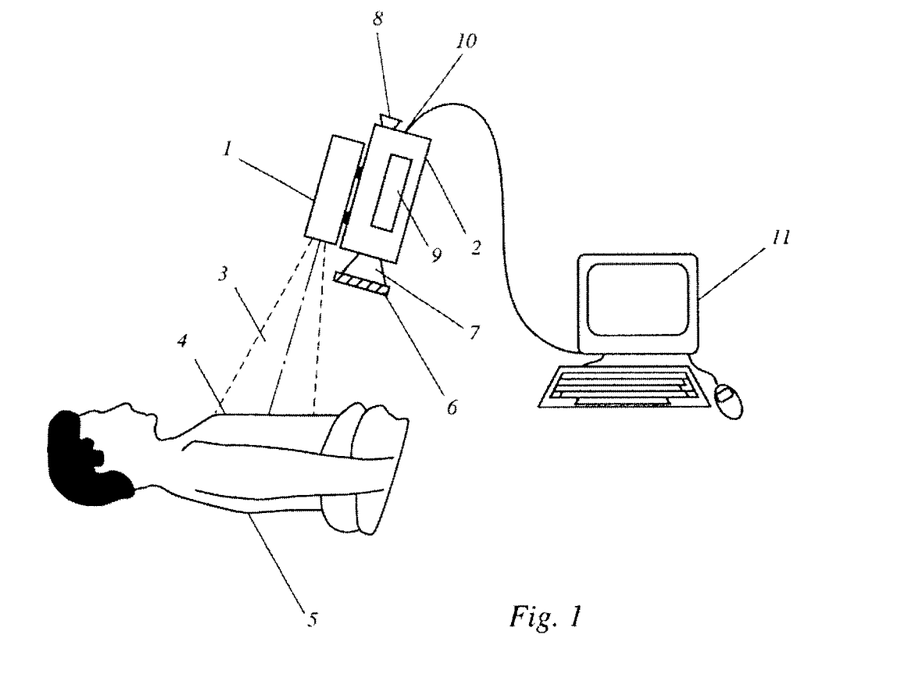
FIG. 1 shows schematically a camera system for observing ICG fluorescence.

FIG. 1 shows schematically a device for non-invasively determining blush of myocardial tissue by ICG fluorescence imaging. An infrared light source, for example, one or more diode lasers or LEDs, with a peak emission of about 780-800 nm for exciting fluorescence in ICG is located inside housing 1. The fluorescence signal is detected by a CCD camera 2 having adequate near-IR sensitivity; such cameras are commercially available from several vendors (Hitachi, Hamamatsu, etc.). The CCD camera 2 may have a viewfinder 8, but the image may also be viewed during the operation on an external monitor which may be part of an electronic image processing and evaluation system 11.

A light beam 3, which may be a divergent or a scanned beam, emerges from the housing 1 to illuminate an area of interest 4, i.e. the area where the blush of myocardial tissue is to be measured. The area of interest may be about 10 cm×10 cm, but may vary based on surgical requirements and the available illumination intensity and camera sensitivity.

A filter 6 is typically placed in front of the camera lens 7 to block excitation light from reaching the camera sensor, while allowing fluorescence light to pass through. The filter 6 may be an NIR long-wave pass filter (cut filter), which is only transparent to wavelengths greater than about 815 nm, or preferably a bandpass filter transmitting at peak wavelengths of between about 830 and about 845 nm and having a full width at half maximum (FWHM) transmission window of between about 10 nm and 25 nm in order to block the excitation wavelength band. The camera 2 may also be designed to acquire a color image of the area of interest to allow real-time correlation between the fluorescence image and the color image.

In general, the surgeon is interested in how well the blood is perfusing the tissue in the area within a region of interest (ROI). Blood vessels visible in the image typically include major blood vessels, e.g., arteries; however, arterial blood flow may not be of interest to the surgeon when considering perfusion of the surrounding myocardial tissue. Because these blood vessels may have either a higher or a lower brightness in the image, depending on the phase of the cardiac cycle, contributions from blood vessels to the measured image brightness may alter the myocardial blush grade by skewing the average image brightness upward or downward. In order to obtain a correct value for the myocardial blush, the contributions from the blood vessels must be eliminated before the blush grade is computed.

Figure 2:
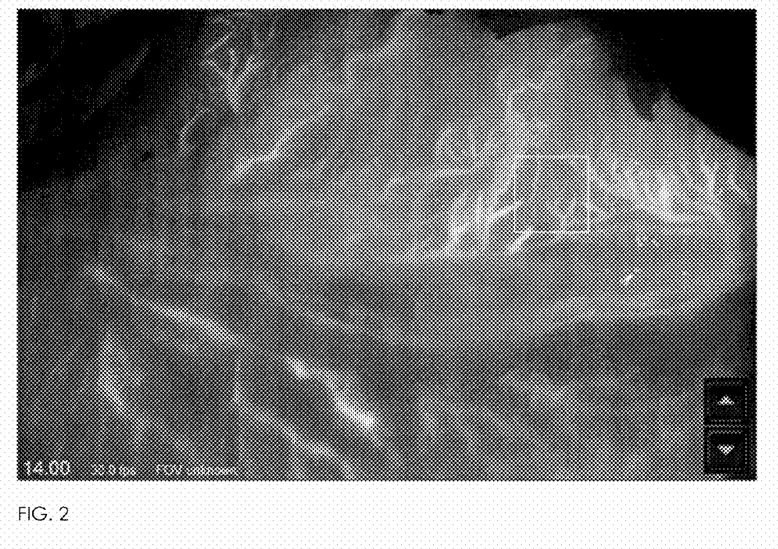
FIG. 2 shows an ICG fluorescent cardiac image, with the rectangle delineating a static ROI on the imaged area.

FIG. 2 shows a typical ICG fluorescent image of a heart showing blood vessels and myocardial tissue, with a rectangle delineating a static ROI on the imaged area. The ROI is static, meaning that it does not track tissue movement when the heart is beating. This simplifies the computation, while the results computed with the method of the invention are robust and largely insensitive to tissue movement.

To compute meaningful average blush intensity within the delineated static ROI, the following needs to be taken into consideration:

1 The selected area of the anatomy within the ROI should consist primarily of myocardial tissue, while minimizing the effects from blood vessels, clips, etc. that appear in the ROI and may move in and out of the ROI when the heart is beating.
2 The measured myocardial blush value should be substantially independent of the size of the ROI in the selected area of the anatomy.

Figure 3:
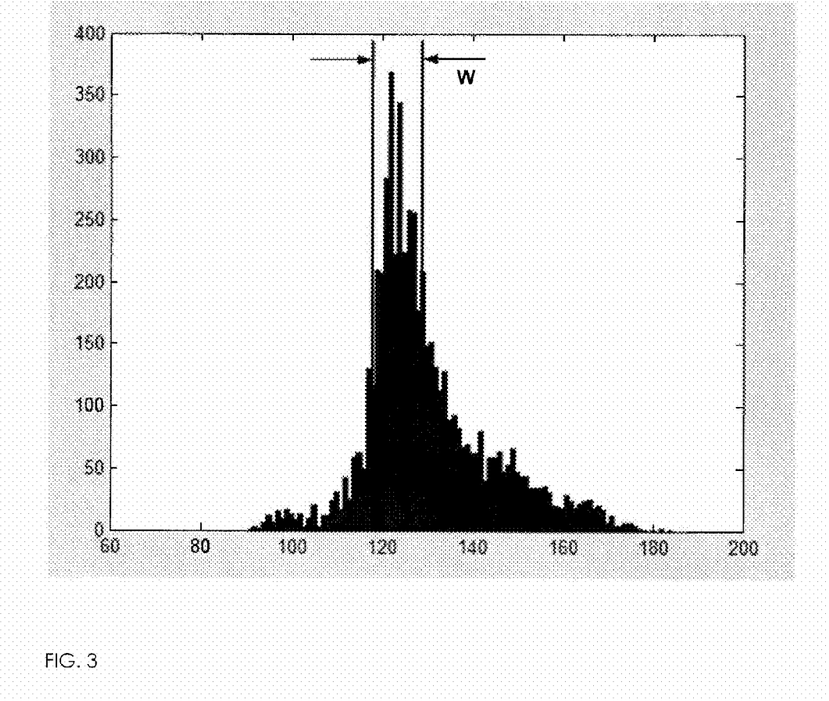
FIG. 3 shows a histogram of the number of pixels (vertical axis) as a function of the measured brightness value (horizontal axis)

According to one embodiment illustrated in FIG. 3, a histogram of the grayscale intensity values in the ROI of FIG. 2 is generated. The horizontal axis of the histogram represents the full range of intensity values arranged in bins (e.g., $2^8=256$ bins for an 8-bit image representing pixel intensities 0 to 255), whereas the vertical axis indicates the number of pixels for each intensity value in a bin. In comparison, a histogram of a 12-bit image would have $2^{12}=4,096$ intensity bins.

A sliding window W is applied across the abscissa, and the smallest set of adjacent histogram bins containing in excess of a predetermined percentage of the total intensity is determined. In the illustrated example, a percentage value of 50% is selected as criterion for the bins to be included, although other values can be selected as long as these selected values exclude outliers and provide a reliable assessment of the blush. For the histogram depicted in FIG. 3, the smallest set of adjacent histogram bins containing at least 50% of the intensity counts results in a window W which is 12 bins wide and includes the intensity values between 120 and 131.

The average intensity for the static ROI is then computed using only the values inside the window determined above, i.e., the number of pixels in a bin multiplied with the intensity in that bin and summed over all bins within the window W.

This approach excludes the intensity outliers (both low and high intensity values) from the computation of the average intensity representing the myocardial blush value in the ROI. In other words, only intensity values between 120 and 131 within the ROI are included in the subsequent calculation.

Figure 4:
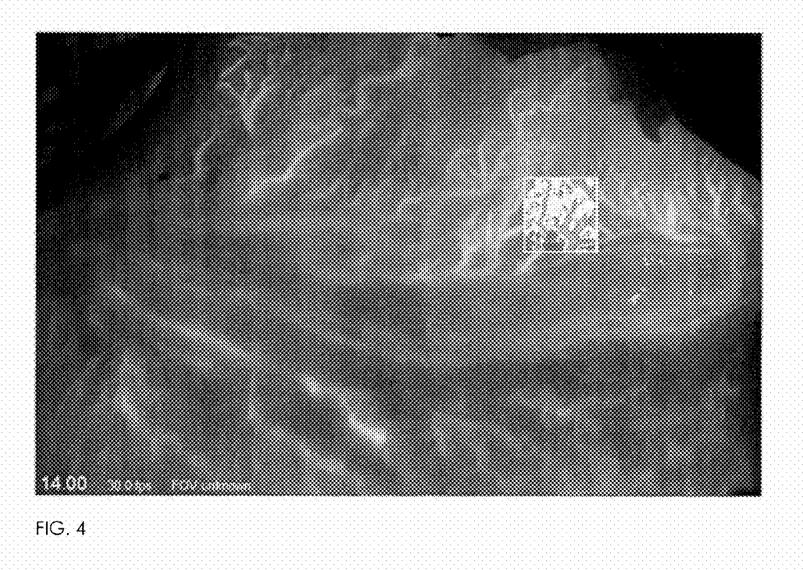
FIG. 4 shows the location of pixels within the static ROI that contain at least 50% of the intensity counts over the smallest set of adjacent histogram bins in FIG. 3.

FIG. 4 shows the location of pixels within the static ROI with intensity values within the window W (according to the selection criterion that about 50% of the intensity values are located within the window W). The bright areas indicate the pixels included. As can be seen, the area with the included pixels need not be contiguous.

Figure 5:
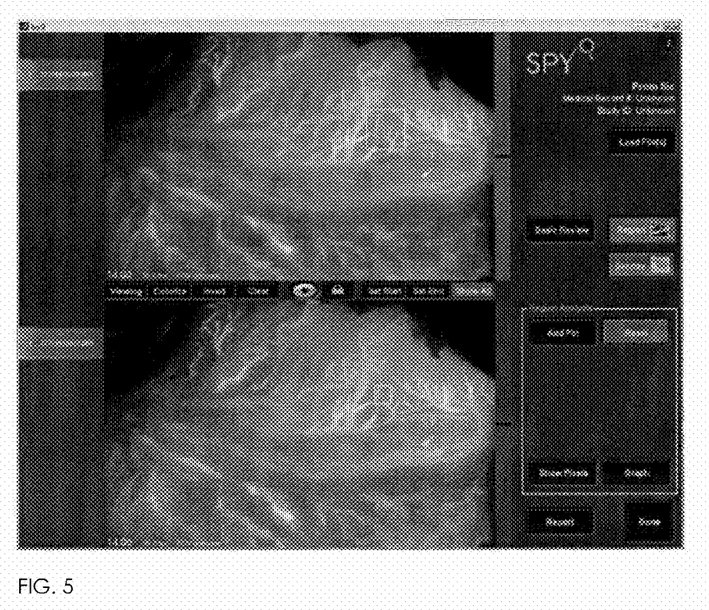
FIG. 5 shows the static ROI of FIG. 2 (top image) and a smaller static ROI (bottom image) located within the ROI of the top image.

FIG. 5 shows the static ROI of FIG. 2 (top image) and a smaller static ROI (bottom image) located within the ROI of the top image. The smaller ROI includes less arterial blood vessels.

Figure 6:
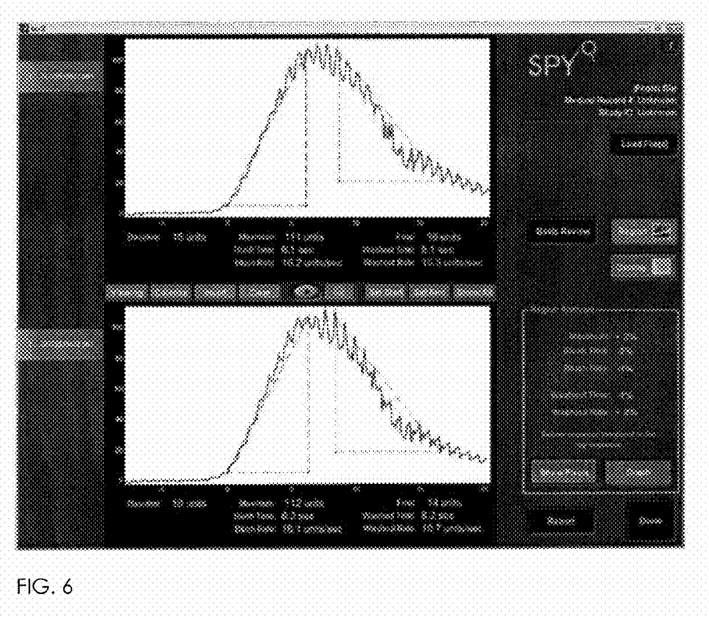
FIG. 6 shows the time dependence of the computed average intensity for the pixels highlighted in FIG. 4 (top image) and for the smaller static ROI of FIG. 5 (bottom image) taken over a 28 second time period.

FIG. 6 shows schematically the computed average intensity for both the static ROIs of FIG. 5 taken over a 28 second time interval. The elapsed time (from the point an increase in the intensity was detected, in seconds) is plotted on the abscissa, and the average intensity for the static ROI (in arbitrary units) is plotted on the ordinate. The two curves match within about 1-3 percent.

The maximum blush is approximately 112 [arb. units], the blush rate measured over about 6.1 sec from about zero blush to about the maximum value is in linear approximation about 16.2 [arb. units]/sec, and the washout rate measured over about 6.1 sec from about the maximum blush value to about 15-20% blush is in linear approximation about 10.5 [arb. units]/sec. Blush appears to increase and decrease (washout) exponentially, so the linear curve fitting described above should be considered only as an approximation. Other characteristic values of the curves of FIG. 6, such as a maximum slope or a curve fit with an exponential rise and decay time may also be used.

The average blush and the blush and washout rates obtained with this technique agree with the blush values perceived by the naked eye.

The static ROI algorithm described above does not rely on image tracking and is generally insensitive to the motion artifacts because of the exclusion of outliers. It is computationally fast and works well with both low and high contrast images.

Figure 7:
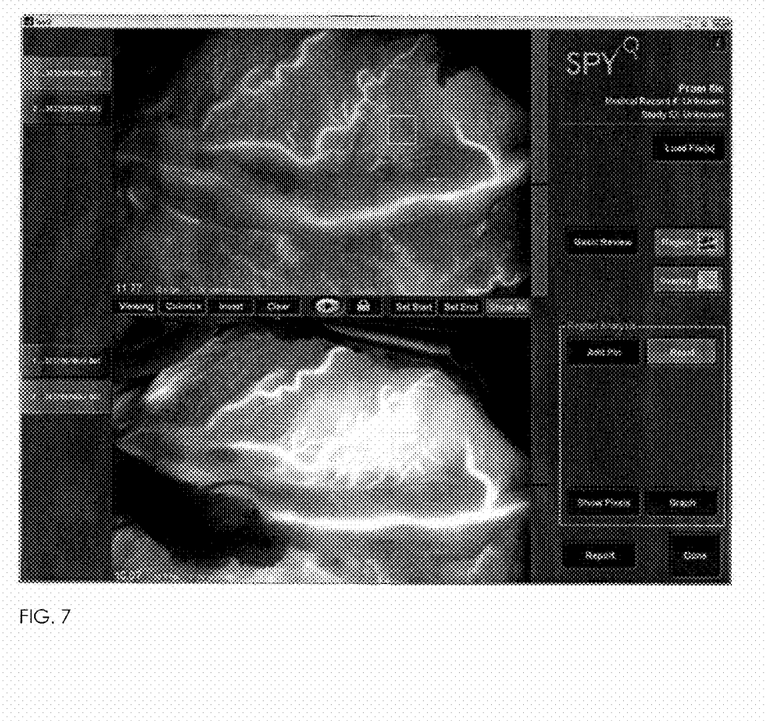
FIG. 7 shows an ICG fluorescent cardiac image with a static ROI before a surgical procedure (top image), and after the procedure (bottom image)

FIG. 7 shows pictures of the heart before and after a surgical procedure has been performed on the heart. A comparison of the blush determined with the aforedescribed method of the invention before and after the procedure can be used to determine whether perfusion has improved as a result of the procedure.

For obtaining reliable and meaningful results, the ICG dosage, illumination level and camera sensitivity settings should be adjusted so that the detector in the camera does not saturate when areas in the image, such as arteries, reach their maximum intensity. If the camera nevertheless does saturate, the user needs to decide whether the computed blush rate and washout rate are likely to represent the actual rates, had the detector not saturated.

Two approaches are proposed for comparing image data obtained before and after the procedure: (1) comparing the blush and washout rates before and after the procedure; and (2) comparing the elapsed time from blood vessel peak intensity to maximum blush on images taken before and after the procedure.

With the first approach, a time series of fluorescence images of the anatomy is acquired before (top image of FIG. 7) and after the surgical procedure (bottom image of FIG. 7)

by, for example, injecting a bolus of ICG dye. Only one of the time series of images is shown. A ROI is delineated in each of the images in approximately the same area of the anatomy. The average intensity of the blush is then determined in each of, or in a subset of, the fluorescence images in the time series with the method of the invention described above with reference to the histogram of FIG. 3, which excludes outliers, such as arteries. The average ROI intensity from each image in the time series is normalized to the baseline average intensity of the ROI in the first frame to correct for residual ICG that may have remained in the system.

Figure 8:
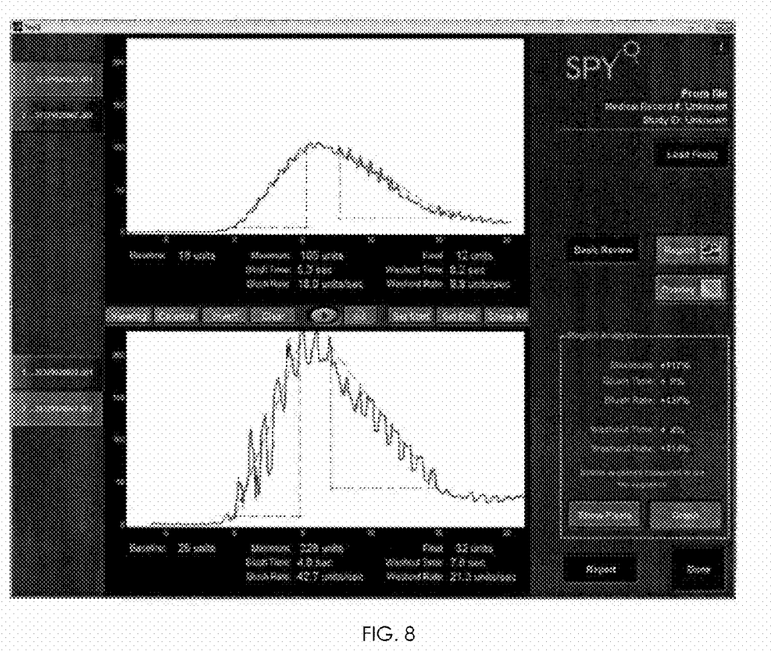
FIG. 8 shows the time evolution of the average blush intensity for the pixels within the ROI of FIG. 7 before the procedure (top image) and after the procedure (bottom image) taken over a 28 second time period.

FIG. 8 shows schematically the computed average intensities (about 50% of the intensity values are located within the window W of a histogram corresponding to the histogram of FIG. 3) for the static ROIs of FIG. 7 taken over a 28 second time interval. The top graph represents values before the procedure and the bottom graph values after the procedure. The elapsed time (from the point an increase in the intensity was detected, in seconds) is plotted on the abscissa, and the average intensity for the static ROI (in arbitrary units) is plotted on the ordinate. The broken line through the data represents a smoothed curve of the raw data. This helps to mask variation in the measurement due to motion caused by the cardiac cycle or respiration and serves as a visual guide for assessing the blush rate and washout rate. As mentioned above, saturation of the sensor should be avoided, because saturation would make an absolute determination of the slope impractical.

The blush and washout rates are determined from the corresponding slopes of straight lines connecting the 5% and 95% points in the average intensity curves, i.e., the start of blush is taken as the time at which the intensity rises above the baseline by 5% of its maximum value, and the 95% point is the time at which the intensity reaches 95% of its maximum value. The same applies to the determination of the washout rate, with the 5% point at the end of washout determined with reference to the final values, which may be higher than the initial 5% point due to residual IeG remaining in the myocardial tissue. The 5% and 95% thresholds are heuristic thresholds used to discount for any noise that may appear in the image both before the blush appears, and as it nears its maximum value.

It will be understood that the slope of the straight lines represents an average rate, and that the rate can also be determined from a least-square curve fit or by selecting points other than 5% and 95%, as described in the illustrated example.

As indicated in FIG. 8, the blush rate following the procedure is about 43 units/sec, compared to about 18 units/sec before the procedure, representing an improvement of about 140%. Likewise, the washout rate following the procedure is about 21 units/sec, compared to about 10 units/sec before the procedure, representing an improvement of more than 100%. Greater perfusion (blush) and washout rates suggest faster movement of blood and greater maximum blush suggests a greater volume of ICG-bound blood in the tissue and are hence clear indicators of improved perfusion through the tissue.

With the second approach, perfusion is determined from the time of maximum blood vessel (artery) intensity to maximum myocardial blush. For example, for cardiac surgery, the surgeon would draw two regions of interest (ROI), a first region covering the coronary artery feeding blood to the heart and a second region covering myocardial tissue receiving blood from that artery. The maximum myocardial blush is determined from the histogram of the first region, as described above (FIG. 8). Peak intensity of the blood vessel may advantageously be determined from an area in the first region showing pixel intensity greater than that of the surrounding tissue. For example, a histogram of the grayscale intensity values may be constructed for the first region and a sliding window W applied across the abscissa, wherein the smallest set of adjacent histogram bins containing a predetermined percentage, for example about 20%, of the pixels with the highest intensity. The lower percentage of pixels included in the computation of the average blood vessel intensity than for myocardial tissue gives the user some flexibility in drawing a larger ROI over the vessel to make the result less sensitive to lateral movement in the vessel during image acquisition.

It will be understood that the first and second regions need not be separate, but may 20 overlap or even be identical, as long as the fluorescence signals from the blood vessels and the myocardial tissue can be clearly separated in the histogram.

It has been observed that before the procedure, the myocardial area may reach maximum blush two seconds after the coronary artery reaches maximum fluorescence intensity. After the procedure, it may only take one second for the myocardial blush to reach maximum blush after the coronary artery reaches maximum fluorescence intensity following the vessel reaching maximum. This finding would lead to the conclusion that cardiac function has improved.

As mentioned above, a blood vessel may move laterally during image acquisition which may make it more difficult to reliably determine the fluorescence intensity, for example during ICG imaging, of a coronary artery. The proposed method provides a means for tracking the movement of the vessel by determining several, typically three, lines which follow the contour of a segment of interest of the blood vessel and approximately span the width of the vessel.

According to the method, features or edges in the image are determined by filtering using a convolution with the Laplacian-of-a-Gaussian kernel. The detected edges may be enhanced (thickened) by defining the edge by a width of at least two pixels. Both the original and the edge-enhanced images are stored.

Figure 9:
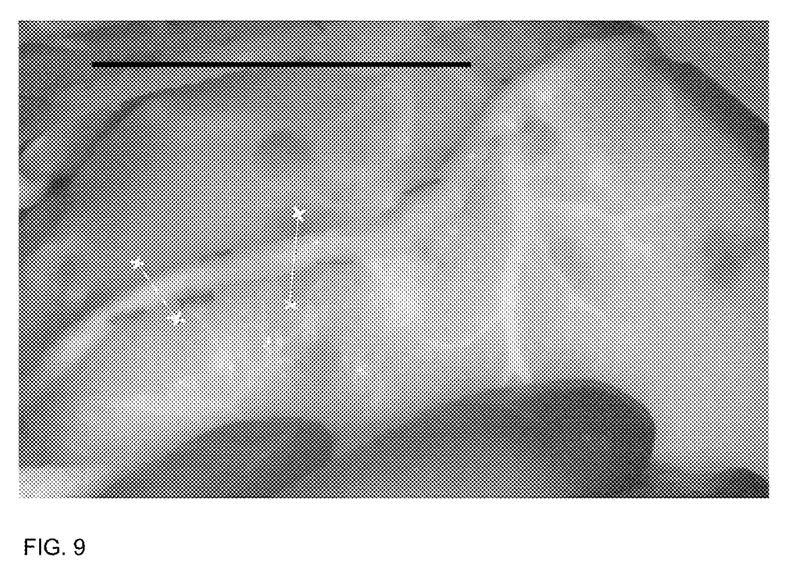
FIG. 9 shows delineation of a segment of a blood vessel for analysis with the method of the invention.
Figure 10:
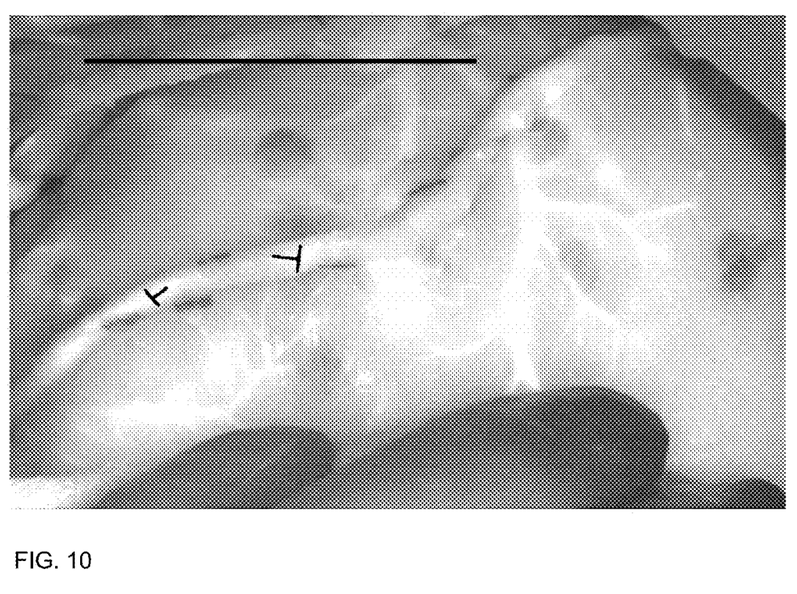
FIG. 10 shows the delineated segment of FIG. 9 with lines terminating at the vessel walls and line normals at the longitudinal end points.
Figure 11:
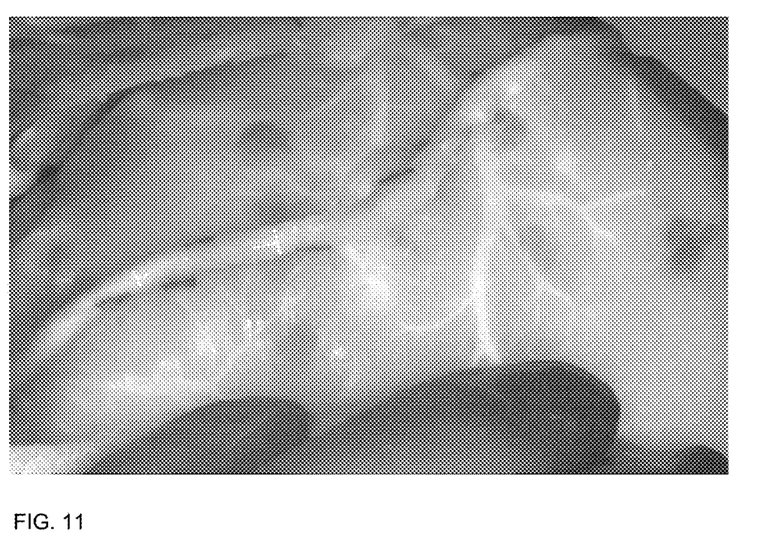
FIG. 11 shows the vessel walls and line normals at the longitudinal end points of FIG. 10 with proper orientation.

Referring now to FIGS. 9 and 10, an operator delimits the segment of the vessel of interest by drawing two lines across the vessel, for example with a computer mouse (FIG. 9). The system then uses the previously determined edge information to detect the segment of each line located between the vessel edges and the mid-point of that segment, which is necessarily also the mid-point of the vessel, and constructs a line normal to each line segment (FIG. 10). Thereafter, the system aligns two line normals with the major longitudinal axis of the vessel (FIG. 11).

Figure 12:
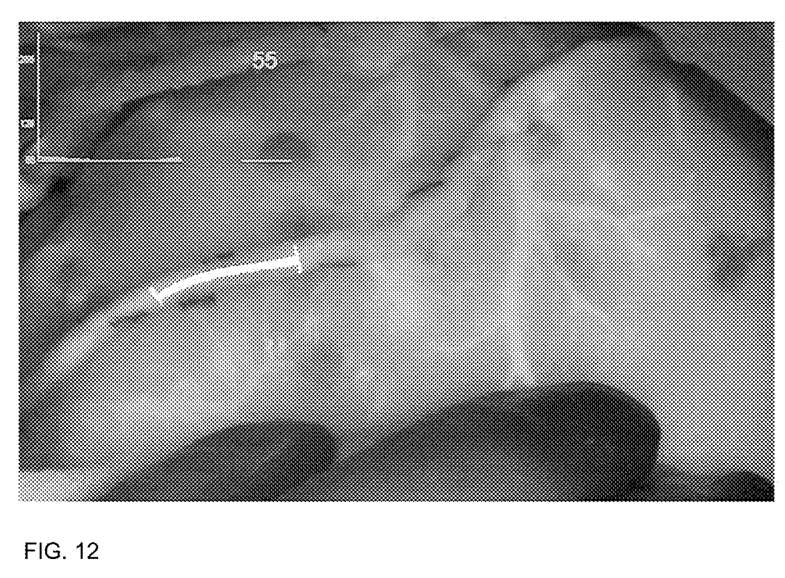
FIG. 12 shows splines connecting the longitudinal end points of FIG. 11 and a longitudinal intensity profile (upper left corner) taken before a procedure.

Next, the system constructs a series of 3 parallel lines, for example cubic spline, of approximately equal length joining the two ends of the segment of interest. However, a greater or lesser number of lines can be used. The lines have at their respective end points the same slope as the respective line normals. Three exemplary lines which approximately span the width of the vessel are shown in FIG. 12. The pixel intensity is sampled at points of each line along the longitudinal axis of the vessel. Preferably, intensities are averaged across the three lines at each location along the longitudinal axis to produce an average vessel intensity at each location in the vessel. As indicated in the insert at the top left corner of FIG. 12, the average intensity in the vessel segment is approximately 55, substantially independent of the longitudinal location in the vessel.

The process is then repeated for the time series of images frame-by-frame, while making sure that the positions match from one frame to the next.

Figure 13:
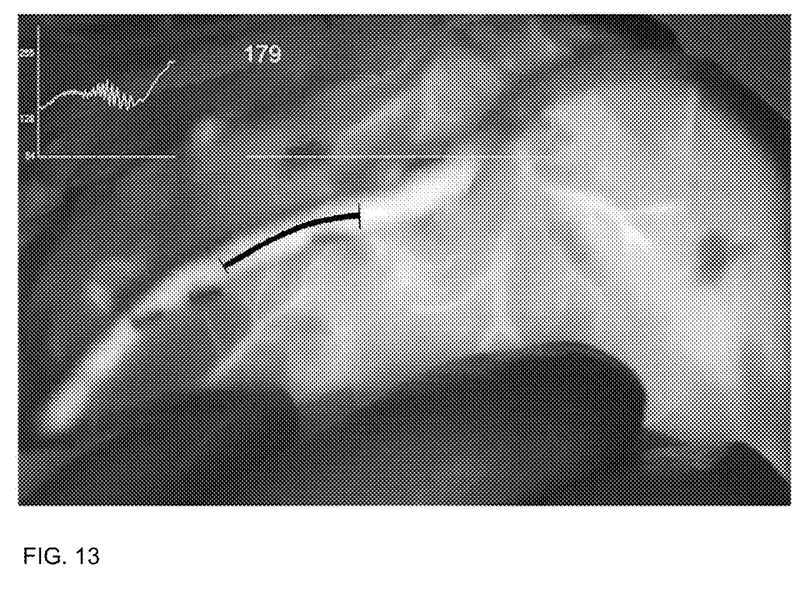
FIG. 13 shows splines connecting the longitudinal end points together with a longitudinal intensity profile (upper left corner) and the time dependence of the intensity profile (upper right corner) taken after a procedure.

FIG. 13 illustrates a final frame in the image sequence processed in this manner. The insert at the top left corner of FIG. 13 shows, as in FIG. 12, the averaged pixel intensity along the three lines. The segment now fluoresces noticeably stronger with an average intensity in the vessel segment of approximately 179. The insert at the top right corner of FIG. 13 shows the change in the average intensity for all of the processed time-ordered frame sequence of images. The "fill time" of the blood vessel can be calculated from the slope of the latter curve (pixel intensity vs. time).

The preceding concepts can be extended to develop quantitative indices useful for intraoperative assessment of blood flow in surgical flaps and for identifying vascular compromise.

Assuming that there is a peak having maximum fluorescence, the following metrics can be computed from the image sequence. If there is no peak, there is likely total arterial occlusion in the flap.

$I'_{In}$ is a measure for the rate of change of increasing perfusion with time as evidenced by the rate of ICG ingress or wash-in.

$I'_{Out}$ is a measure for the rate of change of decreasing perfusion with time after reaching maximum fluorescence intensity as evidenced by the rate of ICG egress or wash-out.

Each of the measures may be taken on a flap either pre- and post-operatively or, once the flap is in place, the measures may be taken from the flap and from adjacent native tissue. With $I'_{in-Pre}$ being the rate of ICG ingress measured on either adjacent native tissue or on the flap pre-operatively, $I'_{in-Post}$ being the rate of ICG ingress measured on the flap post-operatively, Similarly, $I'_{Out-Pre}$ being the rate of ICG egress measured on either adjacent native tissue or on the flap pre-operatively, and $I'_{Out-Post}$ being the rate of ICG egress measured on the flap post-operatively, the Wash-in Ratio $WR_{in}$ can be defined as:

$$WR_{In} = I'_{in-Post}/I'_{in-Pre}$$

and the Wash-out Ratio $WR_{Out}$ can be defined as:

$$WR_{Out} = I'_{Out-Post}/I'_{Out-Pre}.$$

$WR_{In}$ and $WR_{Out}$ will be close to 1.0 in cases with normal vascular conditions.

$WR_{In}$ will be significantly less than 1.0 in cases of arterial spasm or partial arterial occlusion. This metric will vary inversely to the degree of arterial spasm or partial arterial occlusion; the amount by which this metric is less than 1.0 will correlate with increased arterial spasm or arterial occlusion.

$WR_{Out}$ will be significantly less than 1.0 in cases of venous congestion. This metric will vary inversely to the degree of venous congestion; the amount by which this metric is less than 1.0 will correlate with increased venous congestion.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling within the spirit and scope of the appended claims.

What is claimed is:

1. A method for determining perfusion in myocardial tissue using fluorescence imaging, comprising the steps of:
    defining a static region of interest (ROI) in an image of the myocardial tissue;
    measuring fluorescence intensity values of image elements (pixels) located within the ROI; and
    determining a blush value from an average of the intensity values of image elements located within a smallest contiguous range of image intensity values containing a first predefined fraction of a total measured image intensity of all image elements within the ROI.

2. The method of claim 1, wherein the smallest range of contiguous image intensity values is determined from a histogram of a frequency of occurrence of the measured image intensity values.

3. The method of claim 1, wherein the first predefined fraction is between 70% and 30%, preferably between 60% and 40%, and most preferably at about 50%.

4. The method of claim 1, wherein blush values are determined over a predefined period of time.

5. The method of claim 4, wherein the blush values are determined continuously over the predefined period of time.

6. The method of claim 4, further comprising determining a blush rate from a slope of the time-dependent blush values.

7. The method of claim 4, further comprising determining a washout rate from a slope of the time-dependent blush values.

8. The method of claim 1, further comprising
    defining a second static ROI in the image of the myocardial tissue, with the second ROI including an arterial blood vessel, and
    determining a measure of peak intensity of the arterial blood vessel from a total intensity of intensity values of image elements located within a smallest contiguous range of high image intensity values containing a second predefined fraction of a total measured image intensity of brightest image elements within the second ROI.

9. The method of claim 8, wherein the second predefined fraction is approximately 20%.

10. The method of claim 8, further comprising determining an outcome of a procedure by comparing an elapsed time between a maximum blush value and maximum measure of perfusion before the procedure and an elapsed time between a maximum blush value and maximum measure of perfusion after the procedure.

* * * * *